United States Patent
Kakiyama et al.

(10) Patent No.: US 11,253,539 B2
(45) Date of Patent: Feb. 22, 2022

(54) ANTITHROMBOTIC MEDICAL MATERIAL USING NICKEL TITANIUM ALLOY

(71) Applicant: Toray Industries, Inc., Tokyo (JP)

(72) Inventors: So Kakiyama, Otsu (JP); Koji Kadowaki, Otsu (JP); Kazuhiro Tanahashi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 107 days.

(21) Appl. No.: 16/637,912

(22) PCT Filed: Sep. 28, 2018

(86) PCT No.: PCT/JP2018/036201
§ 371 (c)(1),
(2) Date: Feb. 10, 2020

(87) PCT Pub. No.: WO2019/065947
PCT Pub. Date: Apr. 4, 2019

(65) Prior Publication Data
US 2020/0215098 A1    Jul. 9, 2020

(30) Foreign Application Priority Data
Sep. 29, 2017 (JP) .................. JP2017-191159

(51) Int. Cl.
| | |
|---|---|
| A61K 31/727 | (2006.01) |
| A61K 47/02 | (2006.01) |
| A61K 47/34 | (2017.01) |
| A61L 33/02 | (2006.01) |
| A61L 33/12 | (2006.01) |
| A61L 31/16 | (2006.01) |
| A61L 31/10 | (2006.01) |
| A61L 31/02 | (2006.01) |
| A61L 31/12 | (2006.01) |
| A61L 33/00 | (2006.01) |

(52) U.S. Cl.
CPC ............ *A61K 31/727* (2013.01); *A61K 47/02* (2013.01); *A61K 47/34* (2013.01); *A61L 31/022* (2013.01); *A61L 31/10* (2013.01); *A61L 31/12* (2013.01); *A61L 31/16* (2013.01); *A61L 33/0011* (2013.01); *A61L 33/0023* (2013.01); *A61L 33/0035* (2013.01); *A61L 33/0076* (2013.01); *A61L 33/022* (2013.01); *A61L 33/12* (2013.01)

(58) Field of Classification Search
None
See application file for complete search history.

(56) References Cited

U.S. PATENT DOCUMENTS

| | | | |
|---|---|---|---|
| 5,843,172 A | 12/1998 | Yan | |
| 9,795,721 B2* | 10/2017 | Kadowaki | ........... A61L 33/0041 |
| 10,709,822 B2* | 7/2020 | Kadowaki | ........... A61L 33/0023 |
| 2002/0018903 A1 | 2/2002 | Kokubo et al. | |
| 2004/0213818 A1 | 10/2004 | Kashiwabara et al. | |
| 2006/0115514 A1 | 6/2006 | Gengrinovitch | |
| 2009/0155622 A1 | 6/2009 | Yoneyama et al. | |
| 2016/0361472 A1 | 12/2016 | Neilan et al. | |
| 2017/0157303 A1* | 6/2017 | Fujita | ................ A61L 33/0011 |
| 2018/0140752 A1 | 5/2018 | Kadowaki et al. | |
| 2018/0344906 A1 | 12/2018 | Kadowaki et al. | |

FOREIGN PATENT DOCUMENTS

| | | |
|---|---|---|
| JP | 10-295823 | 11/1998 |
| JP | 2002-35109 | 2/2002 |
| JP | 4273965 | 6/2009 |
| JP | 2011-200700 | 10/2011 |
| JP | 2017-000744 | 1/2017 |
| WO | 2007/018189 | 2/2007 |
| WO | 2014/136567 | 9/2014 |
| WO | 2015/080176 | 6/2015 |
| WO | 2016/159243 | 10/2016 |
| WO | 2016/190407 | 12/2016 |

OTHER PUBLICATIONS

Firstov (Biomaterials 23(24) 4863-4871 (2002)).*
Extended European Search Report dated Jun. 10, 2021, counterpart of European Application No. 18863589.0.
Chu, C.I., et al., "Graded surface structure in chemically polished NiTi shape memory alloy after NaOH treatment," *Scripta Materialia*, 52(11): pp. 1117-1121, Jun. 2005. https://www.sciencedirect.com/science/article/pii/S1359646205000850/via%3Dihub//aep-abstract-idI2 (Abstract Only).
Komiyama, H., et al., "Neoartherosclerosis: Coronary stents seal atherosclerotic lesions but result in making a new problem of atherosclerosis," *World Journal of Cardiology*, 7(11): pp. 776-783, Nov. 26, 2015. https://www.ncbi.nlm.nih.gov/pmc/articles/PMC4660472/.
Firstov, G.V., et al., "Surface oxidation of NiTi shape memory alloy," *Biomaterials*, 23(24): pp. 4863-4871, Dec. 2002.

* cited by examiner

*Primary Examiner* — Patricia Duffy
*Assistant Examiner* — Garen Gotfredson
(74) *Attorney, Agent, or Firm* — DLA Piper LLP (US)

(57) ABSTRACT

A medical material uses a nickel-titanium alloy wherein a polyelectrolyte has a reduced thickness while a sufficient amount of an antithrombogenic compound for production of a therapeutic effect is supported. The medical material in which a porous surface is formed on a nickel-titanium alloy to allow infiltration of a polyelectrolyte into the pores, to thereby reduce the thickness of the polyelectrolyte exposed on the surface of the nickel-titanium alloy while allowing supporting of a sufficient amount of an antithrombogenic compound due to contribution of the polyelectrolyte infiltrate.

5 Claims, 4 Drawing Sheets

ANTITHROMBOTIC MEDICAL MATERIAL USING NICKEL TITANIUM ALLOY

TECHNICAL FIELD

This disclosure relates to an antithrombogenic medical material using a nickel-titanium alloy.

BACKGROUND

Since metals have both high strength and moldability, metals having high corrosion resistance in physiological environments such as stainless steels, cobalt alloys, and titanium alloys, are utilized as materials of medical equipment (medical devices and medical instruments). In particular, nickel-titanium alloys cannot be replaced by other materials since they have superelasticity, which is a unique characteristic.

Superelasticity is a property with which, after deformation by application of a load within a temperature range of not less than the shape recovery temperature, the original shape can be recovered by removal of the load applied. By controlling the composition and the thermal history during processing, nickel-titanium alloys can be designed such that they have a shape recovery temperature of not more than body temperature. Therefore, they can exert superelasticity in the body.

However, when a nickel-titanium alloy is used as a material of medical equipment which is to be used in contact with blood (more specifically, an artificial kidney, artificial lung, artificial blood vessel, artificial valve, stent, stent-graft, catheter, free-thrombus capture device, angioscope, suture, blood circuit, tube, cannula, blood bag, syringe or the like), a foreign body reaction occurs on the surface of the nickel-titanium alloy, inevitably causing thrombus formation. In existing medical equipment, thrombus formation is suppressed by ingesting an antithrombotic agent (anticoagulant or antiplatelet agent). However, from the viewpoint of the bleeding risk as a side effect, the thrombus formation risk due to discontinuation of medication, burden on the medical economy and the like, there is an increasing demand for medical equipment subjected to antithrombogenic treatment, which medical equipment allows reduction of the dose, or eliminates the requirement, of the antithrombotic agent.

Methods of giving antithrombogenicity to common metallic materials, wherein heparin or a heparin derivative as an anticoagulant is used for coating of, or chemically bound to, a surface of a metallic material, have been reported. Commonly known methods in which heparin or a heparin derivative is used for coating of, or chemically bound to, a surface of a metallic material include: 1) methods in which an ionic complex is formed between an organic cation mixture and heparin or a heparin derivative, and the ionic complex is dissolved in an organic solvent, followed by coating a surface of a metallic material with the resulting solution; 2) methods in which heparin or a heparin derivative is immobilized by covalent bonding or ionic bonding to a functional group introduced to a surface of a metallic material; and 3) methods in which heparin or a heparin derivative is immobilized by covalent bonding or ionic bonding through a polymer immobilized on a surface of a metallic material.

Reported examples of the methods of 1) include a method in which an ionic complex is formed between an organic cation mixture such as quaternary ammonium salt, and heparin or a heparin derivative, and the resulting ionic complex is dissolved in an organic solvent, followed by coating a surface of a metallic material with the resulting solution (JP 4273965 B).

Reported examples of the methods of 2) include a method in which an agent such as heparin is immobilized through a low molecular weight chelate molecule bound by coordinate bonding to a surface of a metallic material (JP 2011-200700 A).

Reported examples of the methods of 3) include a method in which a cationic polymer is immobilized on a surface of a metallic material through a phosphonic acid derivative or a catechol derivative, and then heparin or a heparin derivative is immobilized by ionic bonding to the immobilized cationic polymer (WO 2016/159243).

Further, as a method of providing a metal on which an agent is directly supported, a method in which a porous layer is formed on a surface of a metallic material for supporting an agent thereon (JP 10-295823 A) has been reported.

Reported examples of a method of forming a porous surface on a metallic material include a method in which titanium or a titanium alloy is immersed in an alkaline solution to form a porous layer composed of an alkali titanate (JP 2002-35109 A) and a method in which a nickel-titanium alloy after removal of its oxide film by physical polishing is immersed in 10 N aqueous sodium hydroxide solution to form a layer of sodium titanate ($Na_2TiO_3$) on a surface of a metallic material (C. L. Chu et al., *Scripta Materialia*, 2005, vol. 52, p. 1117-1121).

Further, examples of clinically widely used vascular stents include stents composed only of metals (bare metal stents "BMS") and drug eluting stents on which a thick polymer layer and a cell growth inhibitor are supported on a surface of a BMS for the purpose of suppressing overgrowth of smooth muscle cells ("DES"). Recently, a result of comparison of long-term prognosis between BMS and DES has been reported (H. Komiyama et al., *World Journal of Cardiology*, 2015, vol. 7, p. 776-783).

In the method disclosed in JP 4273965 B, an ionic complex is formed between an organic cation mixture such as quaternary ammonium salt, and heparin or a heparin derivative, and the resulting ionic complex is dissolved in an organic solvent, followed by coating a surface of a metallic material with the resulting solution. Elution of the ionic complex easily occurs upon contact with a body fluid such as blood, to allow production of antithrombogenicity by the heparin or heparin derivative. However, the mixture of organic cations such as quaternary ammonium salt released at the same time may exhibit hemolytic toxicity.

In the method disclosed in JP 2011-200700 A, a chelate molecule containing a functional group capable of binding to a metal by coordinate bonding and a functional group capable of binding to an agent is immobilized on a surface of a metallic material by coordinate bonding, and an agent such as heparin is immobilized through the functional group capable of binding to the agent in the chelate molecule. However, when the chelate molecule has a low molecular weight, the amount of the cationic compound for the coating is small and, therefore, the heparin or heparin derivative cannot be sufficiently supported so that the required antithrombogenicity cannot be obtained. Further, it has been generally known that since a nickel-titanium alloy has an inactive surface, stable immobilization of an amino- or carboxyl-containing chelate molecule on the surface of the nickel-titanium alloy is difficult.

In the method disclosed in WO 2016/159243, heating at a high temperature of not less than 100° C. is necessary to strongly bind the phosphonic acid derivative or the catechol derivative to the surface of the metallic material. When a nickel-titanium alloy is used as the metallic material, it may undergo plastic deformation, or its superelasticity (more specifically, the shape recovery force and the shape recovery temperature) may change during the heating process.

In the method disclosed in JP 10-295823 A, a surface of a metallic material is made porous to allow an agent to be supported thereon without being mediated by a polymer. However, when a water-soluble agent is used, control of the elution behavior of the agent is difficult. There is a description on a method of controlling the elution behavior of the agent by further coating, with a polymer, the surface of the metallic material after the supporting of the agent. However, that method has a problem in that, when the agent is an antithrombogenic compound, a sufficient performance cannot be obtained immediately after placement of the metal in the body.

In the method disclosed in JP 2002-35109 A, the porous layer of the alkali titanate formed on the surface of the titanium suppresses adsorption of fibronectin, which is a coagulation-system protein, and platelets. However, since the coagulation system itself is not controlled, thrombus formation cannot be suppressed. Further, regarding methods of chemically modifying the modified surface of the titanium, no study has been carried out at all.

In the method disclosed in C. L. Chu et al., *Scripta Materialia*, 2005, vol. 52, p. 1117-1121, the surface of the nickel-titanium alloy is modified using an aqueous sodium hydroxide solution aiming at promoting production of an apatite layer in a simulated body fluid. However, regarding methods of chemically modifying the modified surface of the nickel-titanium alloy, no study has been carried out at all.

According to H. Komiyama et al., *World Journal of Cardiology*, 2015, vol. 7, p. 776-783, by placement of a BMS or a DES at a site of vascular occlusion, the restenosis rate immediately after intravascular treatment can be remarkably decreased. However, during the chronic stage, the surface of the BMS or DES is covered with the intima newly formed in the blood vessel, and neoatherosclerosis ("NA") occurs on the intima to generate a new lesion which may be involved in occlusion. Compared to BMS, DES has a significantly shorter period before development of NA. It is therefore thought that the polymer and the agent exposed on the surface of the metallic material may promote NA. In the method disclosed in WO 2016/159243, the method in which a polymer layer is formed on the outer layer in JP 10-295823 A and the like, the surface of the metallic material is thickly coated with a polymer. Therefore, there is a concern that development of NA may be promoted similarly to DES.

It could therefore be helpful to provide an antithrombogenic medical material in which a porous surface is formed on a nickel-titanium alloy, and a polyelectrolyte is allowed to infiltrate into the pores, to reduce the amount of exposed polyelectrolyte while coating the material with a sufficient amount of an antithrombogenic compound.

SUMMARY

We thus provide (1) to (6):

(1) An antithrombogenic medical material comprising:
a nickel-titanium alloy;
a polyelectrolyte bound to a surface of the nickel-titanium alloy; and
an antithrombogenic compound bound to the polyelectrolyte, the antithrombogenic compound having a charge opposite to the charge of the polyelectrolyte;

wherein
Formula (1) is satisfied according to measurement using X-ray photoelectron spectroscopy (XPS), and
Formula (2) is satisfied according to measurement using Auger electron spectroscopy (AES).

$$Ti_{ratio\_XPS} \geq 2 \quad (1)$$

wherein in Formula (1), $Ti_{ratio,\ XPS}$ represents the abundance ratio (atomic percentage) of titanium element to the abundance of total elements as measured by XPS on a surface of the medical material.

$$C_{ratio\_AES} \geq 7 \quad (2)$$

wherein in Formula (2), $C_{ratio,\ AES}$ represents the abundance ratio (atomic percentage) of carbon element to the abundance of total elements on a surface of the medical material subjected to argon ion etching to 20 nm in terms of $SiO_2$.

(2) The antithrombogenic medical material according to (1), wherein the polyelectrolyte is a cationic polymer containing a monomer selected from the group consisting of alkyleneimines, vinylamines, allylamines, lysine, arginine, histidine, protamine, glucosamine, and diallyldimethylammonium chloride.

(3) The antithrombogenic medical material according to (1), wherein the polyelectrolyte is an anionic polymer containing a monomer selected from the group consisting of acrylic acid, α-hydroxyacrylic acid, vinylacetic acid, vinylsulfonic acid, allylsulfonic acid, vinylphosphonic acid, allylphosphonic acid, aspartic acid, and glutamic acid.

(4) The antithrombogenic medical material according to any one of (1) to (3), wherein the antithrombogenic compound is selected from the group consisting of heparin, heparin derivatives, dextran sulfate, polyvinyl sulfonate, polystyrene sulfonate, argatroban, beraprost sodium, ozagrel, and cangrelor.

(5) The antithrombogenic medical material according to any one of (1) to (4), wherein
Formula (3) is satisfied according to measurement using Auger electron spectroscopy (AES), and
the argon ion etching depth is not less than 20 nm in terms of $SiO_2$.

$$O_{ratio}/Max(O_{ratio})=0.5 \quad (3)$$

wherein in Formula (3), $O_{ratio}$ represents the abundance ratio (atomic percentage) of oxygen element to the abundance of total elements on a surface of the medical material subjected to argon ion etching, and Max ($O_{ratio}$) represents the maximum value of $O_{ratio}$.

Since the antithrombogenic medical material has a nickel-titanium alloy whose surface is modified by immersion in an alkaline solution, a polyelectrolyte can be immobilized thereon at a higher density compared to conventional materials. Since the modification involves infiltration of the polyelectrolyte into inner sites (deeper sites) relative to the surface of the nickel-titanium alloy, the amount of the polyelectrolyte exposed on the surface of the nickel-titanium alloy with respect to the total amount of the polyelectrolyte immobilized can be reduced so that the risk of neoatherosclerosis can be reduced while a sufficient amount of an antithrombogenic compound can be supported.

DETAILED DESCRIPTION

Figure 1:
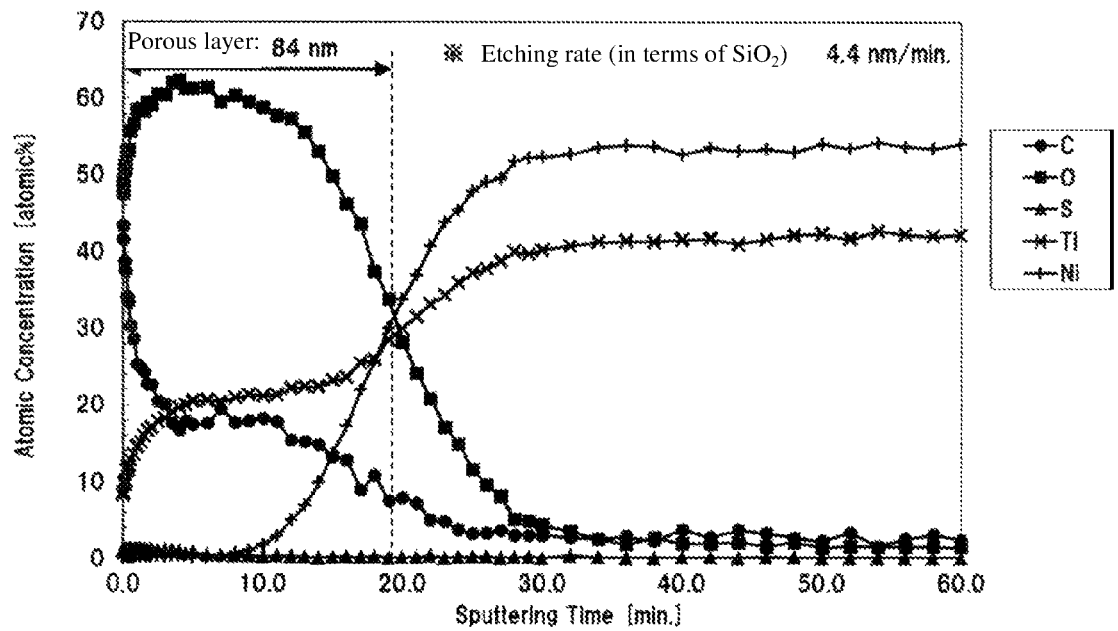
FIG. 1 shows depth profiles in the antithrombogenic medical material of Example 1 as measured using Auger electron spectroscopy (AES).

The antithrombogenic medical material comprises:
a nickel-titanium alloy;
a polyelectrolyte bound to a surface of the nickel-titanium alloy; and
an antithrombogenic compound bound to the polyelectrolyte, the antithrombogenic compound having a charge opposite to the charge of the polyelectrolyte;
wherein
Formula (1) is satisfied according to measurement using X-ray photoelectron spectroscopy (XPS), and
Formula (2) is satisfied according to measurement using Auger electron spectroscopy (AES).

$$Ti_{ratio,XPS} > 2 \quad (1)$$

wherein in Formula (1), $Ti_{ratio, XPS}$ represents the abundance ratio (atomic percentage) of titanium element to the abundance of total elements as measured by XPS on a surface of the medical material.

$$C_{ratio,AES} \geq 7 \quad (2)$$

wherein in Formula (2), $C_{ratio, AES}$ represents the abundance ratio (atomic percentage) of carbon element to the abundance of total elements on a surface of the medical material subjected to argon ion etching to 20 nm in terms of $SiO_2$.

Terms are defined as described below unless otherwise specified.

The antithrombogenic medical material is a material in which an antithrombogenic compound is bound through a polyelectrolyte bound to a surface of a nickel-titanium alloy. Thus, the polyelectrolyte and the antithrombogenic compound are present on the surface of the antithrombogenic medical material, but the polyelectrolyte and the antithrombogenic compound do not necessarily need to be present on the entire surface of the nickel-titanium alloy. However, from the viewpoint of giving antithrombogenicity, the polyelectrolyte and the antithrombogenic compound are preferably present on the entire blood-contacting surface of the nickel-titanium alloy. When the entire surface of the nickel-titanium alloy is in contact with blood, for example, in stents, the polyelectrolyte and the antithrombogenic compound are preferably present on the entire surface of the antithrombogenic medical material.

The antithrombogenic compound means a compound suppressing blood coagulation, and examples thereof include antiplatelet agents that suppress platelet aggregation, and anticoagulants that inhibit blood coagulation which proceeds due to, for example, activation of blood coagulation factors represented by thrombin. By supporting an antithrombogenic compound on a surface of a nickel-titanium alloy, antithrombogenicity can be given thereto. For effective interaction with a polyelectrolyte, the antithrombogenic compound is preferably a water-soluble antithrombogenic compound.

The nickel-titanium alloy is an alloy containing nickel and titanium as major constituent elements. The nickel-titanium alloy preferably contains 50 wt % to 60 wt % nickel element with respect to the total weight, and 40 wt % to 50 wt % titanium element with respect to the total weight. In use as an implant, the grade of the nickel-titanium alloy is more preferably a grade required by the international standard ASTM F2063 or a grade higher than this. Since nickel-titanium alloys exhibit shape memory properties and superelasticity, they can be favorably used to expand an occluded lumen from the inside similarly to stents.

Examples of the shape of the nickel-titanium alloy include, but are not limited to, plates, sheets, rods, wires, microparticle-containing powders, and thin films vapor-deposited on a surface of a polymer or a ceramic. For allowing infiltration of the following polyelectrolyte, the nickel-titanium alloy preferably has a porous layer on a surface.

The polyelectrolyte means a polymer containing in its repeat units an ionizable functional group(s). Based on the type(s) and/or combination of the ionizable functional group(s), the polyelectrolyte can be classified into anionic polyelectrolytes, neutral polyelectrolytes, and cationic polyelectrolytes.

An ionizable functional group herein means a functional group which ionizes in water to exhibit cationic properties or anionic properties. Examples of the ionizable functional group include, but are not limited to, a carboxy group (—COOH), phosphonate group (—PO$_3$H), sulfonate group (—SO$_3$H), hydroxy group (—OH), thiol group (—SH), silanol group (—SiOH), amino group (—NH$_2$), guanidino group (—NH—(C=N)NH$_2$), and imidazoyl group (—C$_3$N$_3$H$_2$).

The polyelectrolyte can be bound to a surface of a nickel-titanium alloy through an ionic bond, hydrogen bond, coordinate bond, or physical adsorption.

The monomers constituting the polyelectrolyte are not limited, and examples of the monomers include alkyleneimines, vinylamines, allylamines, lysine, arginine, histidine, protamine, glucosamine, diallyldimethylammonium chloride, acrylic acid, α-hydroxyacrylic acid, vinylacetic acid, vinylsulfonic acid, allylsulfonic acid, vinylphosphonic acid, allylphosphonic acid, aspartic acid, and glutamic acid. When an anionic antithrombogenic compound such as heparin is immobilized on the surface of the nickel-titanium alloy by ionic bonding, the polyelectrolyte preferably has a cationic functional group. Thus, the polyelectrolyte preferably contains alkyleneimine, vinylamine, allylamine, lysine, arginine, histidine, protamine, glucosamine, or diallyldimethylammonium chloride as a monomer. When a cationic antithrombogenic compound such as argatroban is immobilized on the surface of the nickel-titanium alloy by ionic bonding, the polyelectrolyte preferably has an anionic functional group. Thus, the polyelectrolyte preferably contains acrylic acid, α-hydroxyacrylic acid, vinylacetic acid, vinylsulfonic acid, allylsulfonic acid, vinylphosphonic acid, allylphosphonic acid, aspartic acid, or glutamic acid as a monomer.

The monomers constituting the polyelectrolyte may include a monomer having no ionizable functional group. Examples of the monomer having no ionizable functional group include, but are not limited to, acrylate, methacrylate, acrylamide, methacrylamide, ethylene glycol, propylene glycol, vinyl pyrrolidone, vinyl alcohol, vinyl caprolactam, vinyl acetate, and styrene.

The polyelectrolyte may be either a natural polymer or a synthetic polymer. Further, the polyelectrolyte may be either a homopolymer or a copolymer. When the polyelectrolyte is a copolymer, it may be any of a random copolymer, block copolymer, graft copolymer, and alternating copolymer. When the cationic or anionic antithrombogenic compound is immobilized on the surface of the nickel-titanium alloy by ionic bonding, stronger ionic bonding to the surface of the nickel-titanium alloy can be achieved when a block portion(s) having consecutive monomers containing a charged functional group in the polyelectrolyte interact(s) with the charge of the antithrombogenic compound. Therefore, the polyelectrolyte is more preferably a block copolymer.

The homopolymer herein means a macromolecular compound obtained by polymerization of a single kind of monomers. The copolymer herein means a macromolecular compound obtained by copolymerization of two or more kinds of monomers. The block copolymer means a copolymer having a molecular structure in which at least two kinds of polymers having different repeat units are covalently bound to each other to form a longer chain. The block means each of the "at least two kinds of polymers having different repeat units" constituting the block copolymer.

The polyelectrolyte may be either a linear polymer or a branched polymer. The polyelectrolyte is more preferably a branched polymer since a branched polymer can form more stable ionic bonds at multiple positions with the antithrombogenic compound.

Polyalkyleneimine is preferably used as the polyelectrolyte since it shows a larger amount of adsorption to the anionic antithrombogenic compound based on ionic interaction. Examples of the polyalkyleneimine include polyethyleneimines (PEI), polypropyleneimines, polybutyleneimines, and alkoxylated polyalkyleneimines. PEI is more preferred because of its high charge density.

Specific examples of the PEI include "LUPASOL (registered trademark)" (manufactured by BASF) and "EPOMIN (registered trademark)" (manufactured by Nippon Shokubai Co., Ltd.). The PEI may be a copolymer with other monomers, or may be a modified body. The modified body herein means a polymer having partially undergone, for example, radical decomposition or recombination due to irradiation while the monomer repeat units constituting the polymer are retained.

Polyacrylic acid ("PAA") or polyvinyl acetate is preferably used as the polyelectrolyte since it shows a large amount of adsorption to the cationic antithrombogenic compound based on ionic interaction. PAA is more preferably used because of its high charge density.

When the weight average molecular weight of the polyelectrolyte is too low, there is only a small number of adsorption sites where the antithrombogenic compound can be bound. Therefore, the required pharmacological effect can be hardly obtained. On the other hand, when the weight average molecular weight of the polyelectrolyte is too high, the antithrombogenic compound is encapsulated in the polyelectrolyte so that the pharmacological effect can be hardly produced. Thus, the weight average molecular weight of the polyelectrolyte is preferably 600 to 2,000,000, more preferably 1000 to 1,500,000, still more preferably 10,000 to 1,000,000. The weight average molecular weight of the polyelectrolyte can be measured by, for example, gel permeation chromatography (GPC) or the light scattering method.

The antithrombogenicity of the antithrombogenic compound is produced as anticoagulant action or antiplatelet action. The antithrombogenic compound is selected from the group consisting of, for example, heparin, heparin derivatives, dextran sulfate, polyvinyl sulfonate, polystyrene sulfonate, argatroban, beraprost sodium, ozagrel, and cangrelor.

Among these, examples of an antithrombogenic compound having anticoagulant activity include heparin, heparin derivatives, dextran sulfate, polyvinyl sulfonate, polystyrene sulfonate, and argatroban. Heparin and heparin derivatives are more preferred. The heparin and heparin derivatives are not limited as long as blood coagulation reaction can be inhibited therewith. Examples of the heparin include unfractionated heparin, which is clinically generally and widely used, and examples of the heparin derivatives include low molecular weight heparin, which is also clinically generally and widely used, and heparins having high affinity to antithrombin III.

The low molecular weight heparin is a fraction having a weight average molecular weight of 1000 to 10,000 obtained by subjecting unfractionated heparin to enzyme or chemical treatment followed by performing gel filtration. As the low molecular weight heparin, reviparin, enoxaparin, parnaparin, certoparin, dalteparin, tinzaparin, and pharmaceutically acceptable salts thereof may be preferably used since these have been clinically used.

Examples of an antithrombogenic compound that exhibits antiplatelet action include beraprost sodium, ozagrel, and cangrelor.

The antithrombogenic compounds described above, in water-soluble antithrombogenic compounds, are compounds which are soluble at not less than 1 g in 100 g of water at 25° C., which compounds exhibit antithrombogenicity in a living body.

The antithrombogenic medical material can be favorably used for medical equipment, for example, a medical device or a medical instrument. It is especially preferably used as a material of a stent or a stent-graft.

The method of producing the antithrombogenic medical material is described below. Although the combination of the polyelectrolyte and the antithrombogenic compound is not limited, one example of the method of producing an antithrombogenic medical material using PEI as the polyelectrolyte and using heparin as the antithrombogenic compound is described below.

The method of producing an antithrombogenic medical material preferably comprises, but does not necessarily need to comprise: (1) a step of modifying a surface of a nickel-titanium alloy; (2) a step of immobilizing a polyelectrolyte on the surface of the nickel-titanium alloy; and (3) a step of immobilizing, to the polyelectrolyte, an antithrombogenic compound having a charge opposite to the charge of the polyelectrolyte; for production of a sufficient effect on the surface of the nickel-titanium alloy.

To remove contamination of the surface of the nickel-titanium alloy, a step of washing the nickel-titanium alloy is preferably included before the (1) step of modifying the surface of the nickel-titanium alloy. The step of washing the nickel-titanium alloy herein is not limited as long as adsorbates on the surface of the nickel-titanium alloy can be removed therewith, and examples of the step include washing methods such as ultrasonic washing in an organic solvent, Ar ion etching, acid treatment, base treatment, and ultraviolet irradiation. A plurality of the washing methods described above may be combined to carry out the washing step. The washing step is more preferably a method of washing the surface of the nickel-titanium alloy using piranha solution. Piranha solution is a mixed solution of a hydrogen peroxide solution and sulfuric acid, and has an extremely strong oxidizing power. Thus, by carrying out the washing step of washing the surface of the nickel-titanium alloy using piranha solution, organic substances on the surface of the nickel-titanium alloy can be sufficiently removed.

The (1) step of modifying a surface of a nickel-titanium alloy is a step of allowing infiltration of a polyelectrolyte without changing a macro-shape of the surface of the nickel-titanium alloy that affects adhesiveness to cells or mutagenicity. Examples of the step include, but are not limited to, a step of immersing the nickel-titanium alloy in an aqueous sodium hydroxide solution to form a porous layer on the surface.

When an aqueous sodium hydroxide solution is used for the modification of the surface of the nickel-titanium alloy, the concentration of the aqueous sodium hydroxide solution is not limited as long as the surface of the nickel-titanium alloy can be sufficiently modified. The concentration is preferably 0.5 mol/L to 18 mol/L. From the viewpoint of ease of handling and the reaction time, the concentration is more preferably 1 mol/L to 10 mol/L. The time of the immersion of the nickel-titanium alloy and the temperature during the immersion are not limited as long as the surface of the nickel-titanium alloy can be sufficiently modified. The immersion is preferably carried out at 20° C. to 150° C. for several minutes to several days. When 8 mol/L sodium hydroxide solution is used, the immersion is more preferably carried out at 25° C. to 80° C. for 30 minutes to 24 hours. After forming of the porous layer on the surface, the nickel-titanium alloy may be sufficiently washed with ion-exchanged water or the like to remove sodium hydroxide adhering to the surface of the nickel-titanium alloy.

A mechanism that allows the polyelectrolyte to infiltrate into the surface of the nickel-titanium alloy when the nickel-titanium alloy is immersed in an aqueous sodium hydroxide solution is as described below, although the mechanism is not limited thereto.

The surface of the nickel-titanium alloy before the immersion in the aqueous sodium hydroxide solution is coated with a passivation film having a thickness of several nanometers composed mainly of titanium oxide ($TiO_2$). Upon immersion of the nickel-titanium alloy in the aqueous sodium hydroxide solution, the passivation film is dissolved, leading to exposure of bulk nickel-titanium alloy to the aqueous sodium hydroxide solution. When nickel and titanium are compared in terms of corrosion resistance against an aqueous sodium hydroxide solution, nickel shows better corrosion resistance, while elution of titanium easily occurs to generate ions. On the other hand, nickel is likely to remain on the surface of the nickel-titanium alloy in the form of, for example, nickel hydroxide ($Ni(OH)_2$), which is poorly soluble in an aqueous alkaline solution, while voids are formed at the sites of elution of the titanium ions. Since the nickel hydroxide can be removed by the washing step, a porous layer in which the surface in the pores is coated with an oxide film of titanium oxide is finally formed to allow infiltration of the polyelectrolyte and the antithrombogenic compound.

Examples of the (2) step of immobilizing a polyelectrolyte include, but are not limited to, a method in which a nickel-titanium alloy having a porous layer formed on its surface is immersed in an aqueous solution of the polyelectrolyte. The concentration of the aqueous solution of the polyelectrolyte is preferably 0.1 wt % to 20 wt %, more preferably 1 wt % to 10 wt %.

When the polyelectrolyte contains a primary to tertiary amino group, a quaternary ammonium modification step may be further included for modifying the amino group in the polyelectrolyte into quaternary ammonium to allow exertion of high cationic properties independent of the pH.

When the quaternary ammonium modification step is included, this step may be carried out either before or after the (2) step of immobilizing a polyelectrolyte on the surface of the nickel-titanium alloy. More specifically, after immobilization of the polyelectrolyte on the surface of the nickel-titanium alloy, the alloy may be immersed in a solution containing an alkyl halide compound such as methyl chloride or ethyl bromide, or containing a glycidyl-containing quaternary ammonium salt, to achieve the quaternary ammonium modification. Alternatively, a polyelectrolyte whose amino groups are preliminarily converted to quaternary ammonium may be used for the above step (2).

When the polyelectrolyte does not contain a cationic functional group, a cationic polymer may be immobilized to the polyelectrolyte by covalent bonding to enable binding of an anionic antithrombogenic compound by ionic bonding through the cationic polymer.

For example, when PAA is used as the polyelectrolyte, a covalent bond can be formed by condensation between a carboxyl group of the PAA and an amino group of PEI using a dehydration-condensation agent, although the binding method is not limited thereto.

Examples of the type of the dehydration-condensation agent include, but are not limited to, carbodiimide compounds such as N,N'-dicyclohexyl carbodiimide, N,N'-di-isopropyl-carbodiimide, 1-ether-3-(3-dimethylaminopropyl) carbodiimide, 1-ether-3-(3-dimethylaminopropyl) carbodiimide hydrochloride ("EDC"), 1,3-bis(2,2-dimethyl-1,3-dioxolan-4-ylmethyl)carbodiimide, N-{3-(dimethylamino)propyl-}-N'-ethylcarbodiimide, N-{3-(dimethylamino)propyl-}-N'-ethylcarbodiimide methiodide, N-tert-butyl-N'-ethylcarbodiimide, N-cyclohexyl-N'-(2-morpholinoethyl)carbodiimide, meso-p-toluenesulfonate, N,N'-di-tert-butylcarbodiimide, and N,N'-di-p-tricarbodiimide; and triazine compounds such as 4-(4,6-dimethoxy-1,3,5-triazin-2-yl)-4-methylmorpholinium chloride n-hydrate ("DMT-MM").

Examples of the (3) step of immobilizing an antithrombogenic compound having a charge opposite to the charge of the polyelectrolyte include a method in which a dehydration-condensation agent is used to perform condensation reaction between a functional group contained in the polyelectrolyte and a functional group contained in the antithrombogenic compound to form a covalent bond, to achieve the immobilization, and, when the polyelectrolyte contains a cationic functional group, a method in which an ionic bond is formed between the cationic functional group contained in the polyelectrolyte and an anionic functional group contained in the antithrombogenic compound, to achieve the immobilization. Since the anticoagulant action or the antiplatelet action of the antithrombogenic compound decreases due to the formation of the covalent bond, the method in which an ionic bond is formed to achieve the immobilization is preferred. Specific examples of the method include, but are not limited to, a method in which a nickel-titanium alloy having the polyelectrolyte immobilized thereon is brought into contact with an aqueous solution containing the antithrombogenic compound.

More specifically, the presence of a composition on the surface of the antithrombogenic medical material can be determined by time-of-flight secondary ion mass spectrometry ("GCIB-TOF-SIMS").

Measurement Conditions

Apparatus: TOF.SIMS 5 (manufactured by ION-TOF GmbH)

Primary ion species: $Bi_3^{++}$

Secondary ion polarity: positive or negative

Etching ion: Ar gas cluster ion (Ar-GCIB)

Mass range (m/z): 0 to 1500

Raster size: 300 μm×300 μm

Pixel number (each side): 128 pixels

Post-acceleration: 10 kV

Measured degree of vacuum (before sample injection): not more than $4×10^{-7}$ Pa Primary ion acceleration voltage: 30 kV Pulse width: 5.1 ns Bunching: yes (high mass resolution measurement)

Charge neutralization: no

Pulsed primary ions are radiated to the surface of the antithrombogenic medical material placed in an ultrahigh vacuum, and then secondary ions released from the surface of the antithrombogenic medical material, having a certain amount of kinetic energy, are guided to the time-of-flight mass spectrometer. Since a mass spectrum dependent on the mass of the secondary ions is obtained, organic substances and inorganic substances present on the surface of the antithrombogenic medical material can be identified, and information on the abundance of each substance can be obtained based on its peak intensity. By combined use of an Ar gas cluster ion beam ("GCIB"), depth direction analysis can also be carried out.

For example, when the antithrombogenic compound is heparin, the presence of the heparin on the surface of the antithrombogenic medical material can be confirmed based on detection of at least one kind of peak selected from the group consisting of the $^{80}SO_3^-$ peak, $^{97}SO_4H^-$ peak, $^{71}C_3H_3O_2^-$ peak, and $^{87}C_3H_3O_3^-$ peak, which are peaks for negative secondary ions.

For example, when the polyelectrolyte contains PEI, the presence of the PEI on the surface of the antithrombogenic medical material can be confirmed based on detection of at least one kind of peak selected from the group consisting of the $^{18}NH_4^+$ peak, $^{28}CH_2N^+$ peak, $^{43}CH_3N_2^+$ peak, and $^{70}C_4H_8N^+$ peak, which are peaks for positive secondary ions; and the $^{26}CN^-$ peak and $^{42}CNO^-$ peak, which are peaks for negative secondary ions, by observation by GCIB-TOF-SIMS.

For example, when the polyelectrolyte contains PAA, the presence of the PAA on the surface of the antithrombogenic medical material can be confirmed based on detection of the $^{71}C_3H_3O_2^-$ peak, which is a peak for a negative secondary ion, by observation by GCIB-TOF-SIMS.

In the antithrombogenic medical material, the presence of the porous layer on the surface of the nickel-titanium alloy and the infiltration of the polyelectrolyte into the pores can be confirmed by depth direction analysis using Auger electron spectroscopy ("AES"). AES is a method in which the abundance ratio of a particular element on a surface of a measurement target can be measured as "atomic percentage".

AES Measurement Conditions

Apparatus: SAM-670 type scanning Auger electron spectroscope (manufactured by Ulvac-Phi Inc.)

Acceleration voltage: 10 kV

Sample Current: 20 nA

Sample inclination angle: 30° (the angle of the detector with respect to the sample plane normal)

Measured degree of vacuum: $1×10^{-5}$ Pa

In AES, the surface of the antithrombogenic medical material is irradiated with X-ray, and the energy of Auger electrons generated therefrom is measured. From the resulting binding energy values of bound electrons in the substance, the abundance ratio of each element on the surface of the measurement target can be obtained.

The depth direction analysis using AES described above is a method in which ion etching and AES measurement are repeatedly carried out for the surface of the measurement target, to perform composition analysis while scraping the surface of the measurement target at the atomic level.

The ion species to be used for the ion etching is not limited, and examples thereof include Ar ion etching and GCIB etching. Since a high energy is required for etching a metallic element, Ar ion etching is preferably employed.

Ion Etching Condition

Ion species: $Ar^+$

Acceleration voltage: 2 kV

Sample inclination angle: 30° (the angle of the detector with respect to the sample plane normal)

Etching rate: 4.4 nm/min (in terms of $SiO_2$)

By performing the depth direction analysis using AES on the surface of the measurement target, a depth profile, wherein the relationship between the etching depth and the abundance ratio of a particular element is plotted, can be prepared. The etching depth can be calculated as the product of the etching rate and the etching time. For example, the etching depth after 5 minutes of etching at an etching rate of 4.4 nm/min (in terms of $SiO_2$) is 22 nm (in terms of $SiO_2$).

The infiltration of the polyelectrolyte into the porous layer can be confirmed by comparing the depth profile of titanium element with the depth profile of carbon element obtained by depth direction analysis of the surface of the antithrombogenic medical material. More specifically, when carbon element (derived mainly from the polyelectrolyte) is detected at not less than 7 atomic percent at an etching depth where titanium element (derived mainly from $TiO_2$ in the oxide film) is detected at not less than 10 atomic percent, infiltration of the polyelectrolyte to the etching depth can be confirmed. In Examples, the antithrombogenic medical material described above was shown to satisfy Formula (2) since carbon element was detected at not less than 7 atomic percent on the surface after 20-nm etching in terms of $SiO_2$.

$$C_{ratio,AES} \geq 7 \quad (2)$$

wherein in Formula (2), $C_{ratio,\,AES}$ represents the abundance ratio (atomic percentage) of carbon element to the abundance of total elements on a surface of the medical material subjected to argon ion etching to 20 nm in terms of $SiO_2$.

Since the bulk nickel-titanium alloy does not contain oxygen element, and the porous layer abundantly contains oxygen element derived from the oxide film (mainly $TiO_2$) occupying the surface in the pores, the thickness of the porous layer can be estimated from the depth profile of oxygen element obtained by depth direction analysis of the surface of the antithrombogenic medical material. More specifically, the thickness can be estimated based on the etching depth at which the abundance ratio (atomic percentage) of oxygen element to the abundance of total elements is the half value of the maximum value. In Examples, the antithrombogenic medical material described above was shown to have a porous layer with an argon ion etching depth of not less than 20 nm in terms of $SiO_2$, and to satisfy Formula (3).

$$O_{ratio}/Max(O_{ratio})=0.5 \quad (3)$$

wherein in Formula (3), $O_{ratio}$ represents the abundance ratio (atomic percentage) of oxygen element to the abundance of total elements on a surface of the medical material subjected to argon ion etching, and Max ($O_{ratio}$) represents the maximum value of $O_{ratio}$.

Since the porous layer contains a large amount of $TiO_2$ derived from the oxide film, the thickness of the porous layer can be estimated also from the depth profile of nickel element and the depth profile of titanium element obtained by depth direction analysis of the surface of the antithrombogenic medical material. More specifically, the thickness can be estimated based on the ratio between the abundance ratios (atomic percentages) of nickel element and titanium element along the etching depth, wherein the estimation is based on the etching depth at which this ratio becomes not less than 1. By this measurement, the fact that the antithrombogenic medical material has a porous layer of not less than 20 nm in terms of $SiO_2$ on the surface of the nickel-titanium alloy can be demonstrated.

Since the AES measurement result is easily influenced by contamination of the surface of the measurement target, the measurement target before the measurement needs to be sufficiently washed with an organic solvent or water, and dried.

The porous layer on the surface of the nickel-titanium alloy constituting the antithrombogenic medical material can be directly observed with a scanning electron microscope.

Measurement Conditions
Apparatus: S-5500 (manufactured by Hitachi High-Technologies Corporation)
Acceleration voltage: 5.0 kV
Observation magnification: ×10,000 to ×100,000

When the pore size in the surface layer of the porous layer is too large, blood infiltrates and stays therein to act as an origin of thrombus formation, while when the pore size in too small, the polyelectrolyte and the antithrombogenic compound can be hardly allowed to infiltrate into inner sites (deeper sites) relative to the surface of the nickel-titanium alloy. Thus, the pore size is preferably 1 nm to 1 μm, more preferably 10 nm to 200 nm.

The elemental composition on the surface of the antithrombogenic medical material can be detected also by X-ray electron spectroscopy ("XPS"). XPS is a method in which the abundance ratio of a particular element on a surface of a measurement target can be measured as "atomic percentage". The "atomic percentage" means the abundance of a specific kind of element to the abundance of total elements detected, which is taken as 100, in terms of the number of atoms.

Measurement Conditions
Apparatus: PHI 5000 VersaProbe 2 (manufactured by Ulvac-Phi)
Excitation X-ray: monochromatic AlK α1,2 ray (1486.6 eV)
X-ray diameter: 10 μm
X-electron escape angle: 90° (the angle of the detector with respect to the surface of the antithrombogenic medical material)

The surface of the antithrombogenic medical material herein means the portion from the measurement surface to a depth of about 10 nm as detected under the measurement conditions in XPS wherein the X-electron escape angle, that is, the angle of the detector with respect to the surface of the antithrombogenic medical material, is 90°.

In the XPS, by radiating X-ray to the surface of the antithrombogenic medical material, and measuring the energy of photoelectrons generated therefrom, the binding energy values of bound electrons in the substance can be determined. From the binding energy values, information on the elements on the surface of the antithrombogenic medical material can be obtained, and, from the energy shift of the peak at each binding energy value, information on the valence and the binding state can be obtained. In addition, by using the peak area ratio of each peak, quantification, that is, calculation of the abundance ratios of elements, valences, and binding states, is possible.

More specifically, by obtaining the peak area ratios of all detected elements, and correcting each ratio for the relative sensitivity factor (RSF), the abundance ratio of each element contained in the detection area can be obtained as an atomic percentage. For example, the Ni2p3/2 peak, which indicates the presence of nickel element, appears near a peak top value of the binding energy of 853 eV to 857 eV, and the Ti2p peak, which indicates the presence of titanium element, appears near a peak top value of the binding energy of 453 eV to 460 eV.

Vascular endothelial cells are known to have a surface protected by an anionic coat called glycocalyx, which contains glucosaminoglycan and sialoglycoprotein as major components. The thickness of the glycocalyx is 100 nm to 1000 nm in healthy individuals, and 50 nm to 500 nm in patients with type I diabetes. Therefore, from the viewpoint of preventing the polyelectrolyte from affecting glycocalyx on the surface of endothelial cells, the polyelectrolyte exposed on the surface of the antithrombogenic medical material preferably has a thickness of less than 10 nm. In particular, when the polyelectrolyte is a cationic polymer, the thickness is more preferably less than 5 nm since the polyelectrolyte has strong interaction with the glycocalyx.

In the antithrombogenic medical material, the amount of the polyelectrolyte exposed on the surface of the antithrombogenic medical material is suppressed by allowing infiltration of the polyelectrolyte into the porous layer of the nickel-titanium alloy having the porous layer. Accordingly, it was shown in Examples that, when measurement is carried out by XPS with a photoelectron detection angle of 45°, Formula (1) is satisfied, and that the thickness of the layer of the polyelectrolyte and the antithrombogenic compound exposed on the surface of the antithrombogenic medical material is not more than 5 nm.

$$Ti_{ratio,XPS} > 2 \quad (1)$$

wherein in Formula (1), $Ti_{ratio, XPS}$ represents the abundance ratio (atomic percentage) of titanium element to the abundance of total elements as measured by XPS on a surface of the medical material.

Since the XPS measurement result is easily influenced by contamination of the surface of the measurement target, the measurement target before the measurement needs to be sufficiently washed with an organic solvent or water, and dried.

When the polyelectrolyte contains an anionic functional group, the amount of the anionic functional group contained in the polyelectrolyte immobilized on the surface of the nickel-titanium alloy can be quantified by a staining method using a dye containing a cationic functional group.

Although the type of the dye containing a cationic functional group is not limited, it is preferably a water-soluble dye such as toluidine blue O, malachite green, methylene blue, crystal violet, or methyl violet.

A staining method using toluidine blue O as the dye containing a cationic functional group is described below.

A nickel-titanium alloy having a polyelectrolyte immobilized thereon is immersed in 1 mL of a toluidine blue O solution (1 mg/mL, prepared by dissolving toluidine blue O in a sodium hydroxide solution (pH 10.0)) per 1 $cm^2$ of the surface area of the nickel-titanium alloy, and staining is carried out at 37° C. for 1 hour. The nickel-titanium alloy having the polyelectrolyte immobilized thereon is removed from the staining solution, and then washed three times with a sodium hydroxide solution (pH 10.0), followed by treatment with 50% (v/v) aqueous acetic acid solution at 37° C. for 30 minutes to extract toluidine blue O ionically bonded to an anionic functional group present on the surface of the nickel-titanium alloy having the polyelectrolyte immobilized thereon. For the extraction liquid, the absorbances at 630 nm and 750 nm (reference) are measured using an ultraviolet-visible spectrophotometer (U-3900, manufactured by Hitachi High-Tech Science Corporation), and the resulting difference is obtained as the true absorbance. Based on the true absorbance, the amount of toluidine blue O electrostatically adsorbed to the nickel-titanium alloy having the polyelectrolyte immobilized thereon can be quantified using a separately provided calibration curve.

When the polyelectrolyte contains a cationic functional group, the amount of the cationic functional group contained in the polyelectrolyte immobilized on the surface of the nickel-titanium alloy can be quantified by a staining method using a dye containing an anionic functional group.

Although the type of the dye containing an anionic functional group is not limited, it is preferably a water-soluble dye such as Orange II, methyl orange, methyl red, thymol blue, disulfine blue, lumogallion, hydroxynaphthol blue, and Coomassie brilliant blue.

A staining method using Orange II as a dye containing an anionic functional group is described below.

The nickel-titanium alloy having the polyelectrolyte immobilized thereon is immersed in 1 mL of an Orange II solution (1 mg/mL, prepared by dissolving Orange II in acetate buffer (pH 4.0)) per 1 $cm^2$ of the surface area of the nickel-titanium alloy, and staining is carried out at 37° C. for 1 hour. The nickel-titanium alloy having the polyelectrolyte immobilized thereon is removed from the staining solution, and then washed once with acetate buffer (pH 4.0) and then twice with distilled water, followed by treatment with 1 mM aqueous sodium hydroxide solution at 37° C. for 30 minutes to extract Orange II ionically bonded to a cationic functional group on the surface of the nickel-titanium alloy having the polyelectrolyte immobilized thereon. For the extraction liquid, the absorbances at 482 nm and 550 nm (reference) are measured using an ultraviolet-visible spectrophotometer (U-3900, manufactured by Hitachi High-Tech Science Corporation), and the resulting difference is obtained as the true absorbance. Based on the true absorbance, the amount of Orange II electrostatically adsorbed to the nickel-titanium alloy having the polyelectrolyte immobilized thereon can be quantified using a separately provided calibration curve.

Specific examples of the method of evaluating antithrombogenicity of the antithrombogenic medical material include measurement of the anti-factor Xa activity on the surface of the antithrombogenic medical material.

The anti-factor Xa activity herein is an index indicating the degree of inhibition of the activity of factor Xa, which promotes conversion of prothrombin to thrombin. For example, when heparin or a heparin derivative is used as the antithrombogenic compound, the anti-factor Xa activity can be used as an index of antithrombogenicity. For the measurement of the antithrombin Xa activity, "Test Team (registered trademark) Heparin S" (manufactured by Sekisui Medical Co., Ltd.) may be, but does not necessarily need to be, used.

A particular measurement method for the anti-factor Xa activity using "Test Team (registered trademark) Heparin S" is as described below.

The antithrombogenic medical material (for example, a metal piece of 0.5 cm×1.0 cm) is provided, and washed using physiological saline at 37° C. for 30 minutes. The washed metal piece is reacted according to the procedure for "Test Team (registered trademark) Heparin S" (manufactured by Sekisui Medical Co., Ltd.), and the absorbance at 405 nm is measured using a microplate reader (MTP-300, manufactured by Corona Electric Co., Ltd.), followed by calculating the surface amount based on the anti-factor Xa activity according to the procedure. When the anti-factor Xa activity is too low, the surface amount of the heparin or heparin derivative in the antithrombogenic medical material is small, and the antithrombogenicity of interest can be hardly obtained. More specifically, the anti-factor Xa activity is more preferably not less than 50 $mIU/cm^2$, still more preferably not less than 75 $mIU/cm^2$.

When ethylene oxide gas ("EOG") is used for sterilization of the antithrombogenic medical material, heparin activity on the surface of the antithrombogenic medical material decreases due to the EOG sterilization. Thus, the anti-factor Xa activity before the EOG sterilization is preferably not less than 100 $mIU/cm^2$.

EXAMPLES

Our materials and methods are described below in detail by way of Reference Examples, Examples, and Comparative Examples. However, this disclosure is not limited thereto.

Reference Example 1

A nickel-titanium alloy wire (diameter, 1 mm) was used. As a washing step for the nickel-titanium alloy, ultrasonic washing and washing with piranha solution were carried out. First, the nickel-titanium alloy wire was subjected to ultrasonic washing in hexane, acetone, methanol, and distilled water (two times) in that order, and then to vacuum drying. Subsequently, the wire was immersed in piranha solution for 1 hour, and then subjected to five times of ultrasonic washing in distilled water, followed by vacuum drying. Subsequently, the wire was immersed in 8 mol/L aqueous sodium hydroxide solution, and the reaction was allowed to proceed at 60° C. for 1 hour. The aqueous solution after the reaction was removed, and the wire was washed with ion-exchanged water. By this modification treatment of the nickel-titanium alloy, a nickel-titanium alloy wire having a porous layer on the surface was obtained as Reference Example 1.

Reference Example 2

The wire of Reference Example 1 was immersed in 5.0 wt % aqueous PEI (weight average molecular weight, 750,000; manufactured by SIGMA-ALDRICH) solution, and then the reaction was allowed to proceed at 30° C. for 2 hours, to allow adsorption of PEI on the surface of the wire of Reference Example 1. The aqueous solution after the reaction was removed, and then a step of removing non-adsorbed PEI was carried out by washing with Dulbecco's phosphate buffered saline ("DPBS") and distilled water. By this polymer immobilization treatment, a wire in which PEI is immobilized on the nickel-titanium alloy was obtained as Reference Example 2.

Using Orange II, the amount of adsorption of a dye containing a cationic functional group to the surface of the wire of Reference Example 2 was quantified. The result is shown in Table 1. The amount of Orange II adsorbed to the wire of Reference Example 2 was 23.7 nmol/cm$^2$.

Example 1

The wire of Reference Example 2 was subjected to the following antithrombogenic treatment to produce an antithrombogenic medical material of Example 1.

First, a quaternary ammonium modification step for converting amino groups in the PEI into quaternary ammonium was carried out as follows. The wire of Reference Example 2 was immersed in an aqueous solution of ethyl bromide (manufactured by Wako Pure Chemical Industries, Ltd.) in 1 wt % methanol, and then the reaction was allowed to proceed at 35° C. for 1 hour and then at 50° C. for 4 hours, to modify the PEI with quaternary ammonium. The aqueous solution after the reaction was removed, and the composite material was washed with methanol and distilled water.

Subsequently, an antithrombogenic-compound immobilization step for immobilizing the antithrombogenic compound to the PEI was carried out as follows. The wire of Reference Example 2 after the quaternary ammonium modification of amino groups was immersed in an aqueous solution (pH=4) of 0.75 wt % heparin sodium (manufactured by Organon API Inc.) and 0.1 mol/L sodium chloride, and the reaction was allowed to proceed at 70° C. for 6 hours, to allow ionic bonding of heparin to the PEI. The aqueous solution after the reaction was removed, and the resulting product was washed with distilled water, to produce an antithrombogenic medical material of Example 1.

By quantifying the anti-factor Xa activity using "Test Team (registered trademark) Heparin S", the amount of heparin supported on the antithrombogenic medical material of Example 1 was evaluated. The result is shown in Table 2. The amount of heparin supported after immersion of the antithrombogenic medical material of Example 1 in physiological saline for 30 minutes was 246 mIU/cm$^2$, indicating supporting of a sufficient amount of heparin for production of antithrombogenicity.

By carrying out Ar ion beam etching while performing measurement by Auger electron spectroscopy (AES), the elemental composition of the antithrombogenic medical material of Example 1 along the depth direction was evaluated. The result is shown in FIG. 1. After etching to 20 nm in terms of SiO$_2$, carbon element was detected at 21.7 atomic percent. The etching depth at which the depth profile of oxygen element showed the half value was 84 nm in terms of SiO$_2$. In this example, $C_{ratio,\ AES}$ in Formula (2) is 21.7. Thus, a value higher than 7 was obtained as a result. The etching depth satisfying Formula (3) was 84 nm in terms of SiO$_2$, which corresponds to a depth of not less than 20 nm.

By carrying out measurement by X-ray photoelectron spectroscopy (XPS) with a photoelectron detection angle of 45°, the elemental composition of the surface of the antithrombogenic medical material of Example 1 was evaluated. The result is shown in Table 3. When the photoelectron detection angle is 45°, elements are detected for about 5 nm from the surface of the antithrombogenic medical material. In the antithrombogenic medical material of Example 1, the abundance ratio of titanium element to the abundance of total elements detected from the surface of the antithrombogenic medical material was 3.5 atomic percent. In this example, $Ti_{ratio,\ XPS}$ in Formula (1) is 3.5. Thus, a value higher than 2 was obtained as a result.

A coagulation test was carried out by immersing the material in heparinized human whole blood at 37° C. for 2 hours. No thrombus formation was found at all on the surface of the antithrombogenic medical material of Example 1.

Figure 5:
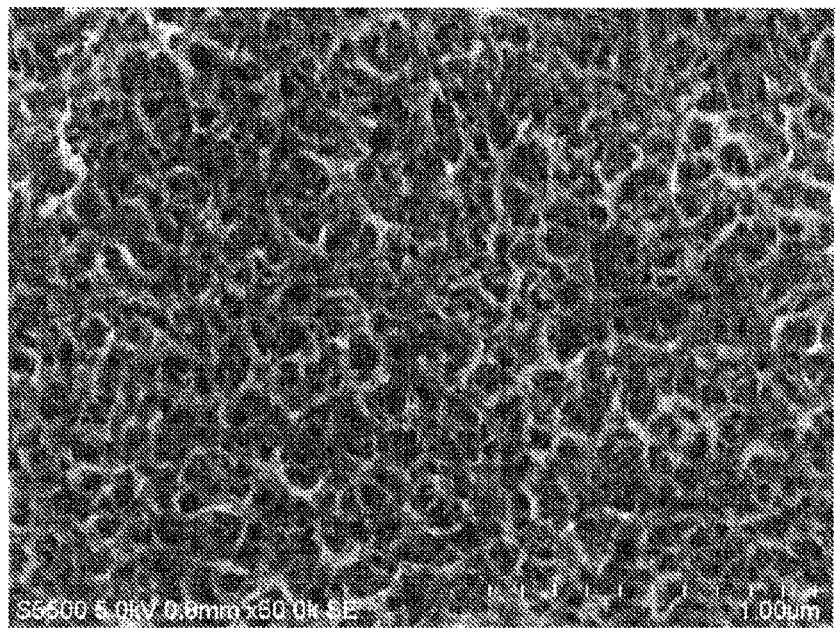
FIG. 5 shows a transmission electron microscope (SEM) image at a magnification of ×50,000 on the surface of the antithrombogenic medical material of Example 1.

SEM observation of the surface of the antithrombogenic medical material was carried out at a magnification of 50,000. The result is shown in FIG. 5. The antithrombogenic medical material of Example 1 showed pores with pore sizes of not more than 100 nm, that is, a porous layer, formed on the entire surface.

Reference Example 3

Modification treatment for the nickel-titanium alloy was carried out in the same manner as in Reference Example 1 except that the time of the immersion in 8 mol/L aqueous sodium hydroxide solution was 6 hours, to obtain a nickel-titanium alloy wire as Reference Example 3, which wire has a porous layer on the surface.

Reference Example 4

Polymer immobilization treatment was carried out in the same manner as in Reference Example 2 except that the wire of Reference Example 3 was used instead of the wire of Reference Example 1, to obtain a wire as Reference Example 4, in which PEI is immobilized on the nickel-titanium alloy.

Using Orange II, the amount of adsorption of a dye containing a cationic functional group to the surface of the wire of Reference Example 4 was quantified. The result is shown in Table 1. The amount of Orange II adsorbed to the wire of Reference Example 4 was 17.5 nmol/cm$^2$.

Example 2

Antithrombogenic treatment was carried out in the same manner as in Example 1 except that the wire of Reference Example 4 was used instead of the wire of Reference Example 2, to obtain an antithrombogenic medical material as Example 2.

By quantifying the anti-factor Xa activity using "Test Team (registered trademark) Heparin S", the amount of heparin supported on the antithrombogenic medical material of Example 2 was evaluated. The result is shown in Table 2. The amount of heparin supported after immersion of the antithrombogenic medical material of Example 2 in physiological saline for 30 minutes was 166 mIU/cm$^2$, indicating supporting of a sufficient amount of heparin for production of antithrombogenicity.

A coagulation test was carried out by immersing the material in heparinized human whole blood at 37° C. for 2 hours. No thrombus formation was found at all on the surface of the antithrombogenic medical material of Example 2.

Reference Example 5

Modification treatment for the nickel-titanium alloy was carried out in the same manner as in Reference Example 1 except that the time of the immersion in 8 mol/L aqueous sodium hydroxide solution was 24 hours, to obtain a nickel-titanium alloy wire as Reference Example 5, which wire has a porous layer on the surface.

Reference Example 6

Polymer immobilization treatment was carried out in the same manner as in Reference Example 2 except that the wire of Reference Example 5 was used instead of the wire of Reference Example 1, to obtain a wire as Reference Example 6, in which PEI is immobilized on the nickel-titanium alloy.

Using Orange II, the amount of adsorption of a dye containing a cationic functional group to the wire of Reference Example 6 was quantified. The result is shown in Table 1. The amount of Orange II adsorbed to the wire of Reference Example 6 was 18.8 nmol/cm$^2$.

Example 3

Antithrombogenic treatment was carried out in the same manner as in Example 1 except that the wire of Reference Example 6 was used instead of the wire of Reference Example 2, to obtain an antithrombogenic medical material as Example 3.

By quantifying the anti-factor Xa activity using "Test Team (registered trademark) Heparin S", the amount of heparin supported on the antithrombogenic medical material of Example 3 was evaluated. The result is shown in Table 2. The amount of heparin supported on the surface after immersion of the antithrombogenic medical material of Example 3 in physiological saline for 30 minutes was 141 mIU/cm$^2$, indicating supporting of a sufficient amount of heparin for production of antithrombogenicity.

Figure 2:
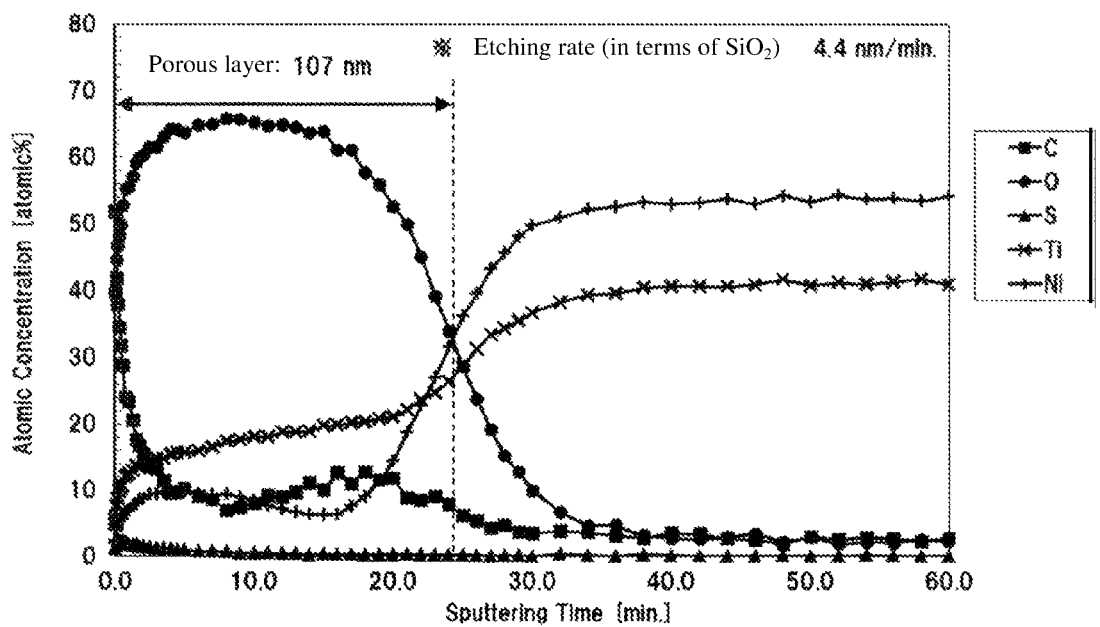
FIG. 2 shows depth profiles in the antithrombogenic medical material of Example 3 as measured using AES.

By carrying out Ar ion beam etching while performing AES measurement, the elemental composition of the antithrombogenic medical material of Example 3 along the depth direction was evaluated. The result is shown in FIG. 2. After etching to 20 nm in terms of $SiO_2$, carbon element was detected at 17.9 atomic percent. The etching depth at which the depth profile of oxygen element showed the half value was 107 nm in terms of $SiO_2$. In this example, $C_{ratio, AES}$ in Formula (2) is 17.9. Thus, a value higher than 7 was obtained as a result. The etching depth satisfying Formula (3) was 107 nm in terms of $SiO_2$, which corresponds to a depth of not less than 20 nm.

By carrying out measurement by XPS with a photoelectron detection angle of 45°, the elemental composition of the surface of the antithrombogenic medical material of Example 3 was evaluated. The result is shown in Table 3. When the photoelectron detection angle is 45°, elements are detected for about 5 nm in the depth direction from the surface of the antithrombogenic medical material. In the antithrombogenic medical material of Example 3, the abundance ratio of titanium element to the abundance of total elements detected from the surface of the antithrombogenic medical material was 2.7 atomic percent. In this example, $Ti_{ratio, XPS}$ in Formula (1) is 2.7. Thus, a value higher than 2 was obtained as a result.

Figure 6:
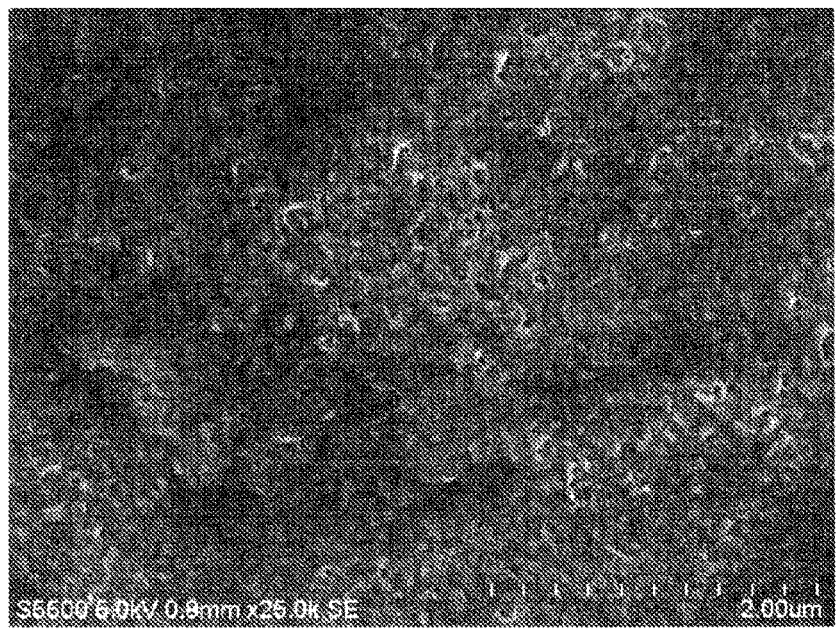
FIG. 6 shows an SEM image at a magnification of ×25,000 on the surface of the antithrombogenic medical material of Example 3.

SEM observation of the surface of the antithrombogenic medical material was carried out at a magnification of 25,000. The result is shown in FIG. 6. A porous layer in which pores having a pore size of about 200 nm are formed was found on the surface of the antithrombogenic medical material of Example 3.

Reference Example 7

Modification treatment for the nickel-titanium alloy was carried out in the same manner as in Reference Example 1 except that the time of the immersion in 8 mol/L aqueous sodium hydroxide solution was 0.5 hour, to obtain a nickel-titanium alloy wire as Reference Example 7, which wire has a porous layer on the surface.

Reference Example 8

Polymer immobilization treatment was carried out in the same manner as in Reference Example 2 except that the wire of Reference Example 7 was used instead of the wire of Reference Example 1, to obtain a wire as Reference Example 8, in which PEI is immobilized on the nickel-titanium alloy.

Using Orange II, the amount of adsorption of a dye containing a cationic functional group to the wire of Reference Example 8 was quantified. The result is shown in Table 1. The amount of Orange II adsorbed to the wire of Reference Example 8 was 12.3 nmol/cm$^2$.

Example 4

Treatment was carried out in the same manner as in Example 3 except that the wire of Reference Example 8 was used instead of the wire of Reference Example 2, to obtain an antithrombogenic medical material as Example 4.

By quantifying the anti-factor Xa activity using "Test Team (registered trademark) Heparin S", the amount of heparin supported on the antithrombogenic medical material of Example 4 was evaluated. The result is shown in Table 2. The amount of heparin supported on the surface after immersion of the antithrombogenic medical material of Example 4 in physiological saline for 30 minutes was 137 mIU/cm$^2$, indicating supporting of a sufficient amount of heparin for production of antithrombogenicity.

Figure 3:
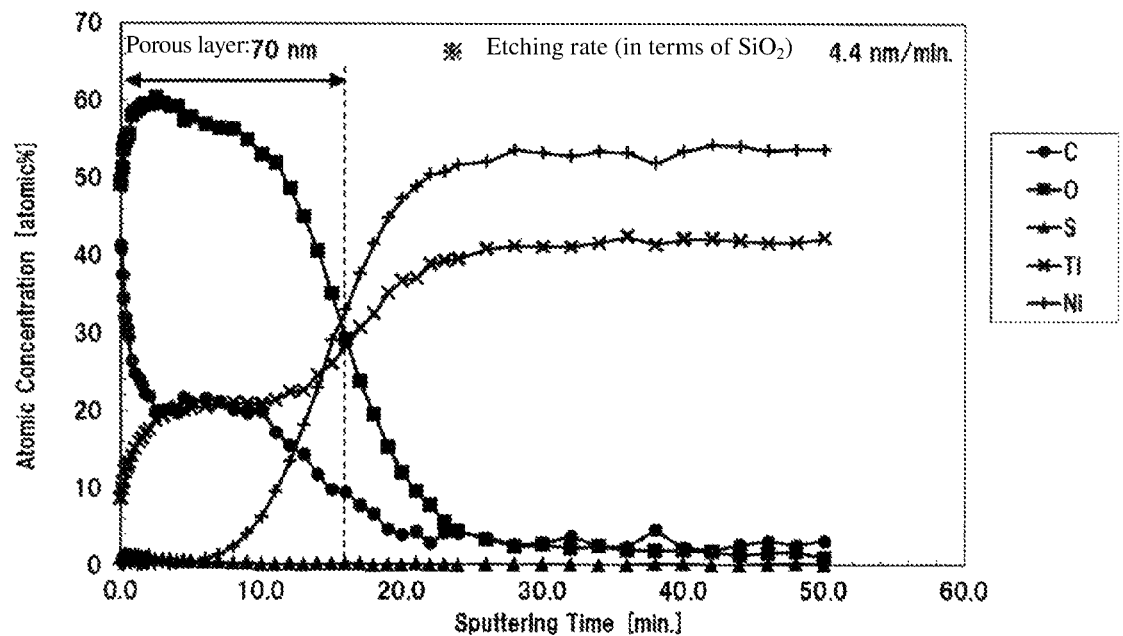
FIG. 3 shows depth profiles in the antithrombogenic medical material of Example 4 as measured using AES.

By carrying out Ar ion beam etching while performing AES measurement, the elemental composition of the antithrombogenic medical material wire of Example 4 along the depth direction was evaluated. The result is shown in FIG. 3. After etching to 20 nm in terms of $SiO_2$, carbon element was detected at 9.66 atomic percent. The etching depth at which the depth profile of oxygen element showed the half value was 70 nm in terms of $SiO_2$. In this example, $C_{ratio, AES}$ in Formula (2) is 9.66. Thus, a value higher than 7 was obtained as a result. The etching depth satisfying Formula (3) was 70 nm in terms of $SiO_2$, which corresponds to a depth of not less than 20 nm.

By carrying out measurement by XPS with a photoelectron detection angle of 45°, the elemental composition of the surface of the antithrombogenic medical material of Example 4 was evaluated. The result is shown in Table 3. When the photoelectron detection angle is 45°, elements are detected for about 5 nm in the depth direction from the surface. In the antithrombogenic medical material of Example 4, the abundance ratio of titanium element to the abundance of total elements detected from the surface of the antithrombogenic medical material was 4.9 atomic percent. In this example, $Ti_{ratio, XPS}$ in Formula (1) is 4.9. Thus, a value higher than 2 was obtained as a result.

Figure 7:
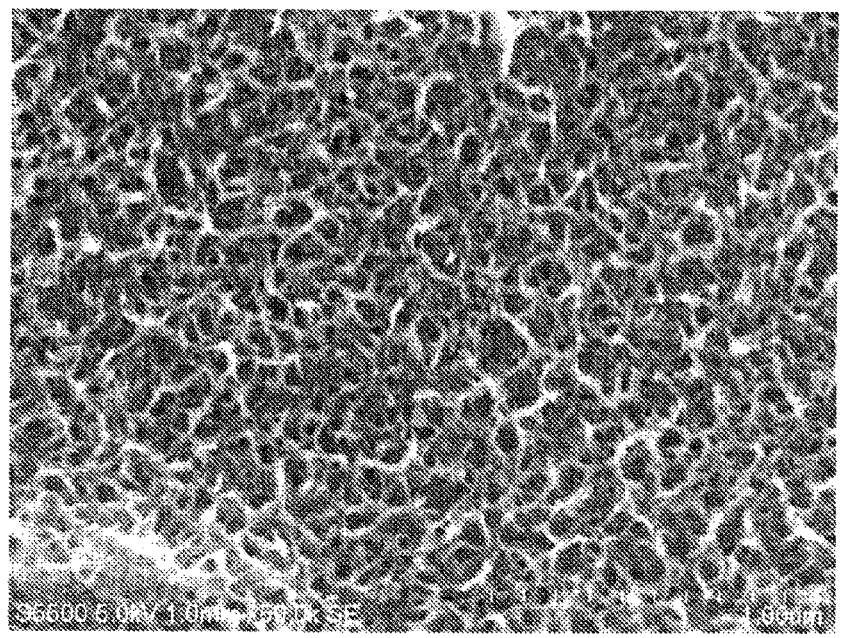
FIG. 7 shows an SEM image at a magnification of ×50,000 on the surface of the antithrombogenic medical material of Example 4.

SEM observation of the surface of the antithrombogenic medical material was carried out at a magnification of 50,000. The result is shown in FIG. 7. The entire surface of the antithrombogenic medical material of Example 4 was found to have a porous layer in which pores having a pore size of not more than 100 nm are formed.

Example 5

The wire of Reference Example 8 was subjected to the following antithrombogenic treatment to produce an antithrombogenic medical material of Example 5.

First, a quaternary ammonium modification step for converting amino groups in the PEI into quaternary ammonium was carried out as follows. The wire of Reference Example 8 was immersed in an aqueous solution of ethyl bromide (manufactured by Wako Pure Chemical Industries, Ltd.) in 1 wt % methanol, and then the reaction was allowed to proceed at 35° C. for 1 hour and then at 50° C. for 4 hours, to modify the PEI with quaternary ammonium. The aqueous solution after the reaction was removed, and the composite material was washed with methanol and distilled water.

Subsequently, an antithrombogenic-compound immobilization step for immobilizing the antithrombogenic compound to the PEI was carried out as follows. The wire of Reference Example 8 after the quaternary ammonium modification of amino groups was immersed in an aqueous solution (pH=4) of 54 international units/mL dalteparin sodium (intravenous dalteparin Na, 5000 units/5 mL "Sawai", manufactured by Sawai Pharmaceutical Co., Ltd.) and 0.1 mol/L sodium chloride, and the reaction was allowed to proceed at 70° C. for 6 hours, to allow ionic bonding of heparin to the PEI. The aqueous solution after the reaction was removed, and the resulting product was washed with distilled water, to produce an antithrombogenic medical material of Example 5.

By quantifying the anti-factor Xa activity using "Test Team (registered trademark) Heparin S", the amount of heparin supported on the antithrombogenic medical material of Example 5 was evaluated. The result is shown in Table 2. The amount of heparin supported on the surface after immersion of the antithrombogenic medical material of Example 5 in physiological saline for 30 minutes was 111 $mIU/cm^2$, indicating supporting of a sufficient amount of heparin for production of antithrombogenicity.

Reference Example 9

The wire of Reference Example 1 was immersed in 1.0 wt % aqueous PAA (weight average molecular weight, 10,000; manufactured by SIGMA-ALDRICH) solution, and then the reaction was allowed to proceed at 30° C. for 2 hours, to allow adsorption of PAA on the surface of the wire of Reference Example 1. The aqueous solution after the reaction was removed, and then a step of removing non-adsorbed PAA was carried out by washing with DPBS and distilled water. By this polymer immobilization treatment, a wire in which PAA is immobilized on the nickel-titanium alloy was obtained as Reference Example 9.

Using toluidine blue, the amount of adsorption of a dye containing an anionic functional group to the surface of the wire of Reference Example 9 was quantified. The amount of toluidine blue adsorbed to the wire of Reference Example 9 was 13.9 $nmol/cm^2$. An antithrombogenic compound having a positive charge can be supported through the negative charge of the PAA. Alternatively, high antithrombogenicity can be given by covalently immobilizing heparin to the PAA, or by converting the terminal carboxyl group of the PAA to a cationic functional group, and then ionically binding heparin to the PAA.

A coagulation test was carried out by immersing the wires of Reference Examples 1, 3, and 5 in heparinized human whole blood at 37° C. for 2 hours. As a result of the coagulation test, all of the wires of Reference Examples 1, 3, and 5 exhibited formation of very firm red thrombi on the entire wire surfaces.

Reference Example 10

A nickel-titanium alloy wire (diameter, 1 mm) was treated in the same manner as in Reference Example 1 except that the immersion in 8 mol/L aqueous sodium hydroxide solution was not carried out at all, and that the modification treatment of the nickel-titanium alloy was not carried out, to obtain a nickel-titanium alloy wire as Reference Example 10.

Comparative Example 1

The nickel-titanium alloy wire of Reference Example 10 was subjected to the same polymer immobilization treatment as in Reference Example 2, to obtain a wire as Comparative Example 1, in which PEI is immobilized on the nickel-titanium alloy.

Using Orange II, the amount of adsorption of a dye containing a cationic functional group to the surface of the wire of Comparative Example 1 was quantified. The result is shown in Table 1. The amount of Orange II adsorbed to the wire of Comparative Example 1 was 2.4 $nmol/cm^2$.

Comparative Example 2

The wire of Comparative Example 1 was subjected to antithrombogenic treatment in the same manner as in Example 1, to obtain an antithrombogenic medical material as Comparative Example 2.

By quantifying the anti-factor Xa activity using "Test Team (registered trademark) Heparin S", the amount of heparin supported on the antithrombogenic medical material of Comparative Example 2 was evaluated. The result is shown in Table 2. The amount of heparin supported after immersion of the antithrombogenic medical material of Comparative Example 2 in physiological saline for 30 minutes was 12 $mIU/cm^2$, indicating failure to support a sufficient amount of heparin for production of antithrombogenicity.

Figure 4:
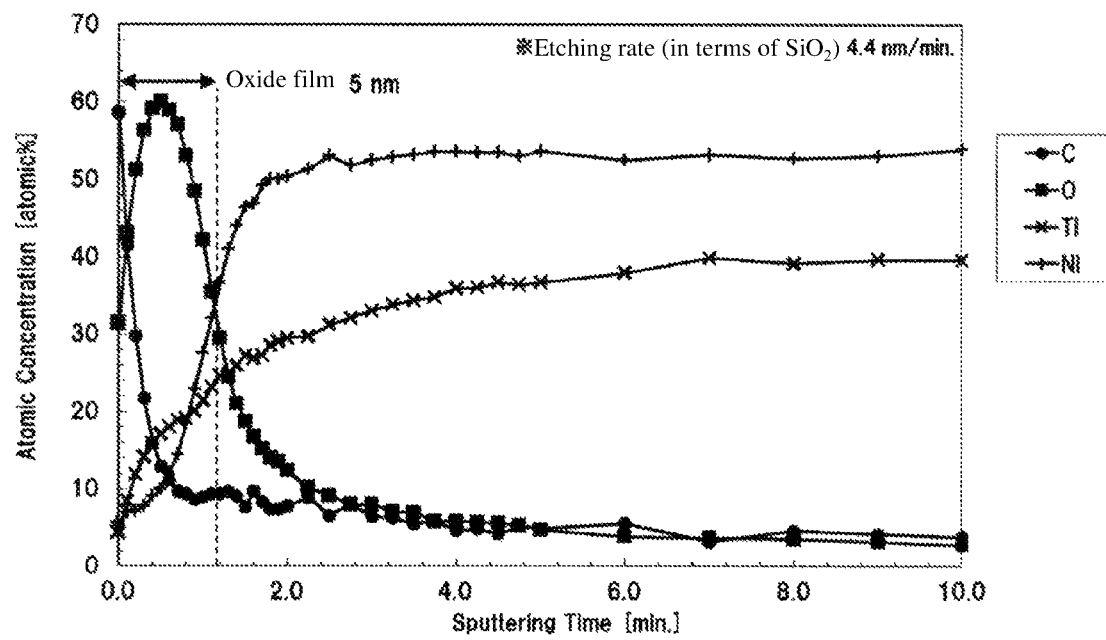
FIG. 4 shows depth profiles in the antithrombogenic medical material of Comparative Example 2 as measured using AES.

By carrying out Ar ion beam etching while performing AES measurement, the elemental composition of the antithrombogenic medical material of Comparative Example 2 along the depth direction was evaluated. The result is shown in FIG. 4. After etching to 20 nm in terms of $SiO_2$, carbon element was detected at 4.3 atomic percent. The etching depth at which the depth profile of oxygen element showed the half value was 5 nm in terms of $SiO_2$. In this example, $C_{ratio,\,AES}$ in Formula (2) is 4.3. Thus, a value lower than 7 was obtained as a result. The etching depth satisfying Formula (3) was 5 nm in terms of $SiO_2$, which corresponds to a depth of less than 20 nm.

By carrying out measurement by XPS with a photoelectron detection angle of 45°, the elemental composition of the surface of the antithrombogenic medical material of Comparative Example 2 was evaluated. The result is shown in Table 3. When the photoelectron detection angle is 45°, elements are detected for about 5 nm in the depth direction from the surface of the antithrombogenic medical material. In the antithrombogenic medical material of Comparative Example 2, the abundance ratio of titanium element to the abundance of total elements detected from the surface of the antithrombogenic medical material was 3.8 atomic percent. In this example, $Ti_{ratio, XPS}$ in Formula (1) is 3.5. Thus, a value higher than 2 was obtained as a result.

Thus, in a method in which a polyelectrolyte is directly bound to a surface of a nickel-titanium alloy without carrying out the (1) step of modifying the surface of the nickel-titanium alloy, an antithrombogenic medical material which exerts sufficient antithrombogenicity cannot be produced.

Comparative Example 3

A nickel-titanium alloy wire (diameter, 1 mm) was used. As a washing step for the nickel-titanium alloy, ultrasonic washing and washing with piranha solution were carried out. First, the nickel-titanium alloy wire was subjected to ultrasonic washing with hexane, acetone, methanol, and distilled water (two times) in that order, and then to vacuum drying. Subsequently, the wire was immersed in piranha solution for 1 hour, and then subjected to five times of ultrasonic washing in distilled water, followed by vacuum drying. Succinyl dopamine ("SUD"), which is represented by General Formula (I), was dissolved in Tris-salt buffer to prepare 1 mM SUD solution. An immersion step was carried out by immersing the washed nickel-titanium alloy wire in the SUD solution at 37° C. to allow formation of a self-assembled monolayer on the surface of the nickel-titanium alloy. After carrying out the immersion overnight, the wire was removed. Thereafter, the wire was washed with water, and then dried under vacuum.

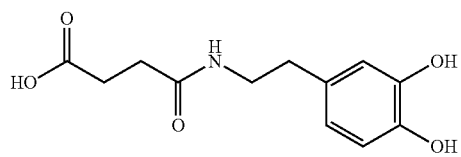

(I)

Subsequently, a step of immobilizing PEI, which is a cationic polymer, to SUD was carried out by immersing the nickel-titanium alloy wire having SUD immobilized thereon in an aqueous solution of 0.5 wt % DMT-MM (manufactured by Wako Pure Chemical Industries, Ltd.) and 5.0 wt % PEI (weight average molecular weight, 750,000; manufactured by SIGMA-ALDRICH), and then allowing the reaction to proceed at 30° C. for 2 hours to covalently bind PEI to SUD by condensation reaction. The aqueous solution after the reaction was removed, and then a step of removing unreacted PEI was carried out by washing with DPBS and distilled water, to obtain a PEI-immobilized nickel-titanium alloy wire as Comparative Example 3.

Using Orange II, the amount of adsorption of a dye containing an anionic functional group to the surface of the PEI-immobilized nickel-titanium alloy wire of Comparative Example 3 was quantified. The result is shown in Table 1. The amount of Orange II adsorbed to the PEI-immobilized nickel-titanium alloy wire of Comparative Example 3 was 7.6 $nmol/cm^2$.

Comparative Example 4

The wire of Comparative Example 3 was subjected to antithrombogenic treatment in the same manner as in Example 1, to obtain an antithrombogenic medical material as Comparative Example 4 by the same method as the method for Sample 17 described in Example 4 of WO 2016/159243.

By quantifying the anti-factor Xa activity using "Test Team (registered trademark) Heparin S", the amount of heparin supported on the antithrombogenic medical material of Comparative Example 4 was evaluated. The result is shown in Table 2. The amount of heparin supported after immersion of the antithrombogenic medical material of Comparative Example 4 in physiological saline for 30 minutes was 70 $mIU/cm^2$.

By carrying out measurement by X-ray photoelectron spectroscopy (XPS) with a photoelectron detection angle of 90°, the elemental composition of the surface of the antithrombogenic medical material of Comparative Example 4 was evaluated. The result is shown in Table 3. When the photoelectron detection angle is 90°, elements are detected for about 10 nm in the depth direction from the surface of the antithrombogenic medical material. In the antithrombogenic medical material of Comparative Example 4, the abundance ratio of titanium element to the abundance of total elements detected from the surface of the antithrombogenic medical material was below the detection limit of XPS. In this example, $Ti_{ratio, XPS}$ in Formula (1) is below the detection limit. Thus, a value lower than 2 was obtained as a result.

Thus, in a method in which a polyelectrolyte is immobilized through a catechol derivative immobilized on a surface of a nickel-titanium alloy instead of carrying out the (1) step of modifying the surface of the nickel-titanium alloy, an antithrombogenic medical material which exerts sufficient antithrombogenicity cannot necessarily be produced even by complete coating of the surface of the nickel-titanium alloy with the polyelectrolyte. Further, since the layer of the polyelectrolyte exposed on the surface of the antithrombogenic medical material has a thickness of not less than 10 nm, the polyelectrolyte affects glycocalyx on endothelial cells.

Comparative Example 5

The wire of Reference Example 10 was immersed in 1.0 wt % aqueous PAA (weight average molecular weight, 10,000; manufactured by SIGMA-ALDRICH) solution, and then the reaction was allowed to proceed at 30° C. for 2 hours, to allow adsorption of PAA on the surface of the wire of Reference Example 10. The aqueous solution after the reaction was removed, and then a step of removing non-adsorbed PAA was carried out by washing with DPBS and distilled water. By this polymer immobilization treatment, a wire in which PAA is immobilized on the nickel-titanium alloy was obtained as Comparative Example 5.

Using toluidine blue, the amount of adsorption of a dye containing an anionic functional group to the surface of the wire of Comparative Example 5 was quantified. The amount of toluidine blue adsorbed to the wire of Comparative Example 5 was 1.0 $nmol/cm^2$.

TABLE 1

| | Amount of adsorption of a dye containing an anionic functional group as measured by Orange II staining ($nmol/cm^2$) |
|---|---|
| Reference Example 2 | 23.7 |
| Reference Example 4 | 17.5 |

TABLE 1-continued

| | Amount of adsorption of a dye containing an anionic functional group as measured by Orange II staining (nmol/cm²) |
|---|---|
| Reference Example 6 | 18.8 |
| Reference Example 8 | 12.3 |
| Comparative Example 1 | 2.4 |
| Comparative Example 3 | 7.6 |

TABLE 2

| | Surface heparin activity measured with Test Team Heparin S (registered trademark) (mIU/cm²) |
|---|---|
| Example 1 | 246 |
| Example 2 | 166 |
| Example 3 | 141 |
| Example 4 | 137 |
| Example 5 | 111 |
| Comparative Example 2 | 12 |
| Comparative Example 4 | 70 |

TABLE 3

| | Detection angle (°) | Abundance ratio of titanium element to the abundance of total elements on the surface of the medical material (atomic percentage) |
|---|---|---|
| Example 1 | 45 | 3.5 |
| Example 3 | 45 | 2.7 |
| Example 4 | 45 | 4.9 |
| Comparative Example 2 | 45 | 3.8 |
| Comparative Example 4 | 90 | Below the detection limit |

INDUSTRIAL APPLICABILITY

Since the antithrombogenic medical material can be coated with a sufficient amount of an antithrombogenic compound while the amount of a polyelectrolyte exposed on the surface of the nickel-titanium alloy can be reduced, it can be used for medical equipment (medical devices and medical instruments) to be placed in the body for a long period in the field of medicine.

The invention claimed is:

1. An antithrombogenic medical material comprising:
a nickel-titanium alloy;
a polyelectrolyte bound to a surface of the nickel-titanium alloy; and
an antithrombogenic compound bound to the polyelectrolyte, the antithrombogenic compound having a charge opposite to the charge of the polyelectrolyte;
wherein
Formula (1) is satisfied according to measurement using X-ray photoelectron spectroscopy (XPS), and
Formula (2) is satisfied according to measurement using Auger electron spectroscopy (AES)

$$Ti_{ratio, XPS} > 2 \quad (1)$$

wherein in Formula (1), $Ti_{ratio, XPS}$ represents the abundance ratio (atomic percentage) of titanium element to the abundance of total elements as measured by XPS on a surface of the medical material $$C_{ratio, AES} \geq 7 \quad (2)$$

wherein in Formula (2), $C_{ratio, AES}$ represents the abundance ratio (atomic percentage) of carbon element to the abundance of total elements on the surface of the medical material after being subjected to argon ion etching to 20 nm in terms of $SiO_2$.

2. The antithrombogenic medical material according to claim 1, wherein the polyelectrolyte is a cationic polymer containing a monomer selected from the group consisting of alkyleneimines, vinylamines, allylamines, lysine, arginine, histidine, protamine, glucosamine, and diallyldimethylammonium chloride.

3. The antithrombogenic medical material according to claim 1, wherein the polyelectrolyte is an anionic polymer containing a monomer selected from the group consisting of acrylic acid, α-hydroxyacrylic acid, vinylacetic acid, vinylsulfonic acid, allylsulfonic acid, vinylphosphonic acid, allylphosphonic acid, aspartic acid, and glutamic acid.

4. The antithrombogenic medical material according to claim 1, wherein the antithrombogenic compound is selected from the group consisting of heparin, heparin derivatives, dextran sulfate, polyvinyl sulfonate, polystyrene sulfonate, argatroban, beraprost sodium, ozagrel, and cangrelor.

5. The antithrombogenic medical material according to claim 1, wherein
Formula (3) is satisfied according to measurement using Auger electron spectroscopy (AES), and
the argon ion etching depth is not less than 20 nm in terms of $SiO_2$, $$O_{ratio}/Max(O_{ratio}) = 0.5 \quad (3)$$

wherein in Formula (3), $O_{ratio}$ represents the abundance ratio (atomic percentage) of oxygen element to the abundance of total elements on a surface of the medical material subjected to argon ion etching, and Max ($O_{ratio}$) represents the maximum value of $O_{ratio}$.

* * * * *